(12) United States Patent
Satulovsky

(10) Patent No.: US 8,645,090 B2
(45) Date of Patent: Feb. 4, 2014

(54) AUTOMATED BASELINE REMOVAL OF SIGNAL

(75) Inventor: Javier E. Satulovsky, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 809 days.

(21) Appl. No.: 12/466,031

(22) Filed: May 14, 2009

(65) Prior Publication Data

US 2010/0292957 A1    Nov. 18, 2010

(51) Int. Cl.
*G01R 13/00* (2006.01)

(52) U.S. Cl.
USPC ........... 702/69; 702/66; 702/179; 702/189; 702/191; 702/194; 702/195

(58) Field of Classification Search
USPC ........... 702/69, 66, 179, 189, 191, 194, 195
See application file for complete search history.

(56) References Cited

U.S. PATENT DOCUMENTS

| | | | |
|---|---|---|---|
| 6,253,162 B1 * | 6/2001 | Jarman et al. | 702/179 |
| 7,219,038 B2 * | 5/2007 | Tracy et al. | 702/189 |
| 7,337,066 B2 | 2/2008 | Neiss | |
| 2007/0110202 A1 * | 5/2007 | Casler et al. | 375/354 |

OTHER PUBLICATIONS

Caballero, et al., "Parabolic-Lorentzian modified Gaussian model for describing and deconvolving chromagraphic peaks," J. Chromatography (2002).*
Ruckstuhl et al., "Baseline subtraction using robust local regression estimation," J. of Quantitative spectroscopy (2001).*
P. Craven et al.,"Smoothing noisy data with spline functions: estimating the correct degree of smoothing by the method of generalized cross-validation", Numer. Math. 1979, 31: pp. 377-403.
K. Kaczmarek et al., "Baseline reduction in two dimensional gel electrophoresis images", ACTA Chromatographica, 2005, 15: pp. 82-96.
J. Kolibal et al, "MALDI-TOF baseline drift removal using stochastic Berstein approximation", J. Appl. Signal Proc. 2006, 63582: pp. 1-9.
CH Reinsch,"Smoothing by Spline Functions", Numer. Math. 1967, 10: pp. 177-183.
A Savitzky et al., "Smoothing and differentiation of data by simplified least squares procedure", Anal.Chem. 1964, 36: pp. 1627-1639.
Y. Sun et al. "ECG signal conditioning by morphological filtering", Computers in Biology and Medicine, 2002, 32(6): pp. 465-479.

* cited by examiner

*Primary Examiner* — Sujoy Kundu
*Assistant Examiner* — Hyun Park

(57) ABSTRACT

A system for estimating a baseline of a signal exhibits a signal generator and a processor. The signal generator is configured to generate a signal exhibiting a plurality of peaks and a baseline. The processor is configured to perform operations including determining an estimator indicating at least one region of the signal that exhibits a peak, determining a weight indicating at least one region of the signal that does not exhibit a peak based on the estimator, and estimating the baseline of the signal based on at least the determined weight.

16 Claims, 14 Drawing Sheets

FIG. 10A
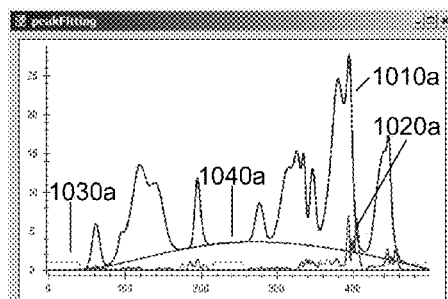
FIG. 10B
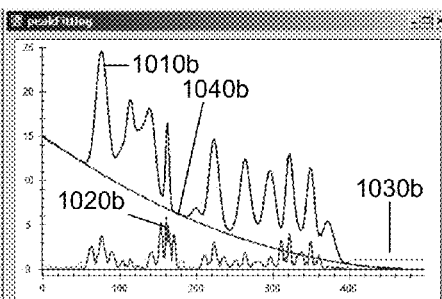
FIG. 10C
FIG. 10D

FIG. 13A 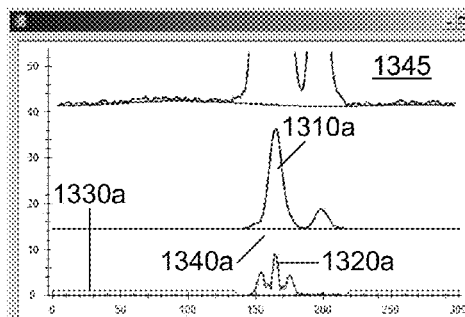 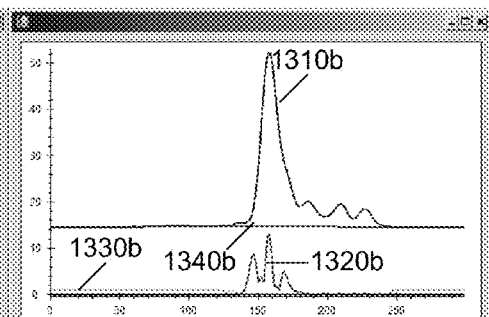 FIG. 13B
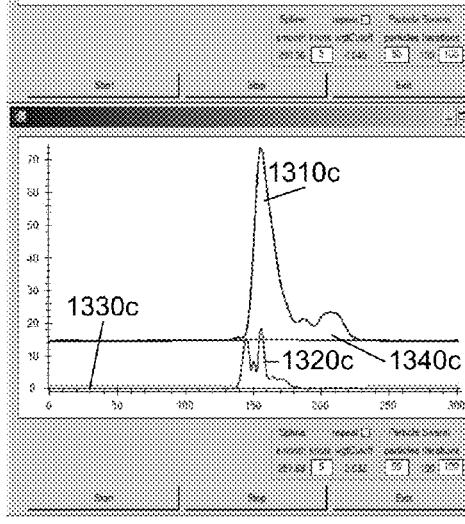 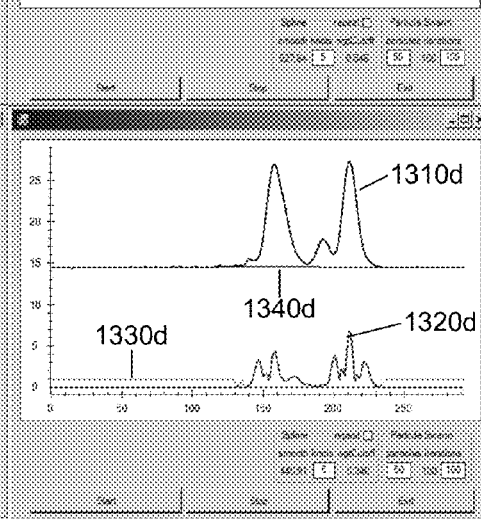
FIG. 13C  FIG. 13D

AUTOMATED BASELINE REMOVAL OF SIGNAL

BACKGROUND

Typically, in gas and liquid chromatography, experimental spectra have background features in addition to the signal of interest. One common source of background features is slow desorption of strongly adsorbed substances previously passed through a column. Baseline drift may also occur in gradient chromatography, particularly when using ultraviolet detection at short wavelengths, because absorbancies of respective solvents begin to change. Other sources of baseline instability are fluctuations in temperature of the column and/or the detector.

Baseline removal is important for applications that involve quantitation, like estimating the amount of each of the compounds generating peaks in the signal. Baseline removal is also important for numerical processing applications performed prior to quantitation, such as estimating the number of peaks present in a signal. Background removal is not only necessary in chromatography, but it is also required to interpret signals in mass spectrometry, for example.

FIG. 1A is a graph showing a signal curve 110 along with a baseline curve 120, and FIG. 1B shows the signal curve 115 with the baseline removed. Referring to FIG. 1A, it is apparent that the baseline curve 120 changes over a longer time frame than the peaks of the signal curve 110. In differential geometry terms, baselines generally are smoother than peaks, as can be seen in FIG. 1A. Therefore, in order to estimate the baseline of a signal, as is necessary, e.g., to determine the amplitudes of the peaks, the smoothness of the baseline curve 120 must be reconciled with the accuracy (or fidelity) with which the base line curve 120 matches the signal curve 110. In other words, the lower bound of the signal curve 110 should be followed as closely as possible without overestimating the baseline curve 120, especially when peaks of the signal curve 110 have a high degree of overlap.

FIG. 2 is a graph showing a signal curve 210 along with an overestimated baseline curve 220, for example, according to a conventional method for baseline estimation. The estimated baseline curve 220 of FIG. 2 is less smooth and follows the signal curve 210 more closely than the baseline curve 120 of FIG. 1A. The asterisks on the baseline curve 220 show instances in which overfitting leads to inaccurate quantitation of the peak areas of the signal curve 210.

Conventionally, digital filters have been used for automated baseline estimation, particularly with respect to periodic signals, such as electrocardiograms. However, use of digital filters tends to introduce artifacts and deform the signal. Another approach to automated baseline estimation is to assume a specified function, usually a polynomial of a certain degree, and to fit the specified function to the signal. However, an actual baseline usually does not mimic a polynomial or a small set of functions from which a user is able to choose.

BRIEF DESCRIPTION OF THE DRAWINGS

The illustrative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

FIGS. 10A-10D are graphs showing estimation of a baseline for a signal having highly overlapped peaks, according to a representative embodiment.

FIGS. 13A-13D are graphs showing estimation of baselines of experimental signals, according to representative embodiments.

DETAILED DESCRIPTION

In the following detailed description, for purposes of explanation and not limitation, illustrative embodiments disclosing specific details are set forth in order to provide a thorough understanding of an embodiment according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as to not obscure the description of the illustrative embodiments. Such methods and devices are clearly within the scope of the present teachings.

In the various embodiments, an automated process provides for estimation and removal of baselines of signals without the need of user intervention. The process is intended for baseline removal a posteriori, that is, after data acquisition has taken place. The process does not require adjustment of parameters and operations having high computational loads can be efficiently parallelized, making it suitable for processing signals consisting of large numbers of points. Also, the process is resistant to overfitting.

Generally, the approach to modeling or estimating a baseline includes rejecting domains of a signal having peaks (peak-containing regions) and then modeling the baseline using the remaining regions (peak-free regions) of the signal. This is achieved, for example, through a binary classification scheme (peak-containing versus peak-free regions) or through a continuous normalized weight function with values that are close to zero in peak-containing regions and values close to one in peak-free regions. However, proper estimation of peak-free regions is difficult, and an estimator based on slope of the signal, for example, is not sufficiently reliable since even a small amount of noise, e.g., noise remaining after de-noising the signal, can confuse the estimator. Representative embodiments therefore include an estimator that naturally takes into account the noise in the signal in determining the peak-free regions of the signal. Then, the peak-free regions are fitted with smoothing splines. In an embodiment, two parameters, e.g., smoothness factor and weight cutoff, have intuitive meanings and may be automatically estimated based on properties of the signal, as discussed below. However, should the user have prior knowledge about the properties of the baseline, these values can be overridden.

Figure 3:
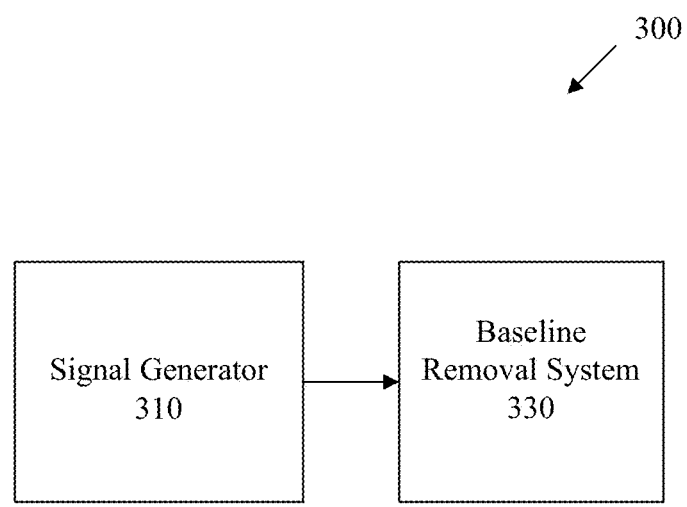
FIG. 3 is a functional block diagram illustrating a system for removing baseline of a signal, according to a representative embodiment.

FIG. 3 is a functional block diagram illustrating a system 300, according to a representative embodiment. The system 300 may be any system for receiving and processing one-dimensional or two-dimensional signals, such as signals produced in accordance with chromatography, mass spectrometry, spectroscopy, electrophoresis, imaging, electronic measurements and the like. The system 300 may represent a liquid chromatography/mass spectrometry (LC/MS) system, for example, which generally combines separation functionality of liquid chromatography with mass analysis ability of mass spectrometry. While the representative embodiments relate to LC/MS applications, the present teachings are more broadly applicable to one-dimensional signals with background features that include an unwanted slowly changing component.

The various "parts" shown in FIG. 3 may be physically implemented using a software-controlled microprocessor, hard-wired logic circuits, or a combination thereof. Also, while the parts are functionally segregated in FIG. 3 for explanation purposes, they may be combined variously in any physical implementation.

Figure 1A:
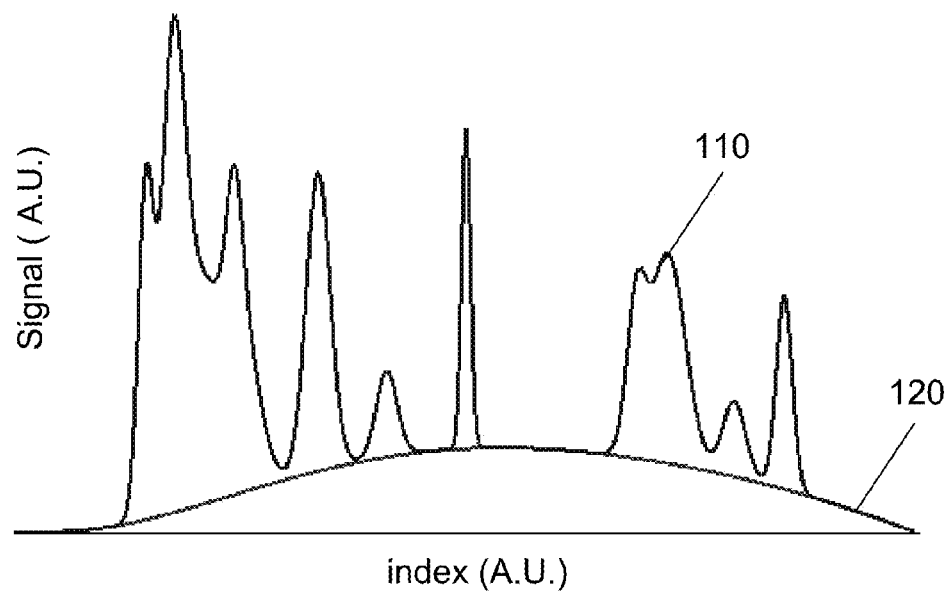
FIGS. 1A and 1B are graphs showing a signal with and without baseline, according to a representative embodiment.
Figure 1B:
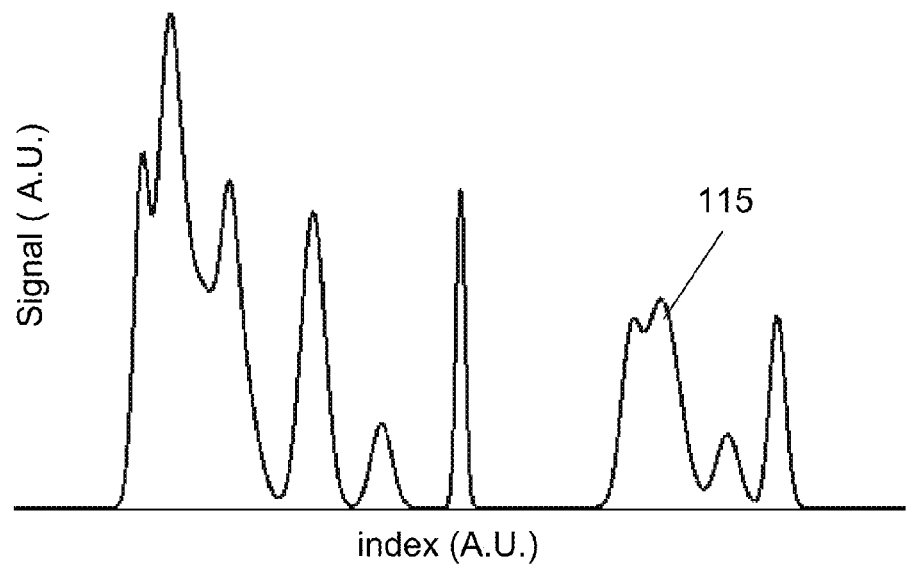

In the depicted representative embodiment, the system 300 includes a signal generator 310 and a baseline removal system 330. The signal generator 310 is configured to generate a signal that exhibits peaks and has a corresponding baseline, as shown for example in FIG. 1A. The signal generator 310 may be embodied as sample separator, for example, which separates samples to provide signals indicating chemical entities included in the samples. Another example of a signal generator 310 is a mass spectrometer, which generates signals having peaks indicating masses corresponding to molecular contents of samples. The signal generator 310 provides (one-dimensional or two-dimensional) signals to the baseline removal system 330, in various embodiments.

The baseline removal system 330 performs processing operations on the received signals, e.g., from sample separations, including the baseline removal process, in accordance with various embodiments discussed below. In various embodiments, the baseline removal system 330 may also execute software that controls the basic functionality of the system 300. The baseline removal system 330 may be implemented as a microprocessor, a digital signal processor (DSP), or the like, or at least in part by hard-wired logic circuits or customizable hardware. As stated above, although depicted separately, the baseline removal system 330 may be included within the sample separator 310, in various embodiments.

Figure 4:
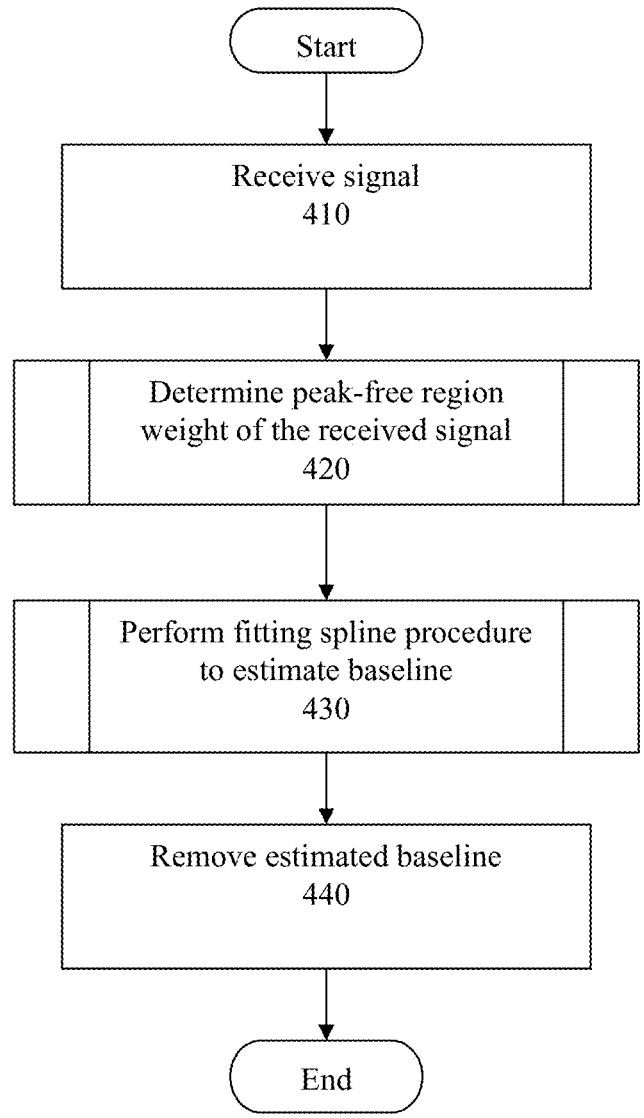
FIG. 4 is a flow diagram of a method for removing baseline of a signal, according to a representative embodiment.

FIG. 4 is a flow diagram illustrating a method for baseline removal, according to a representative embodiment. The various operations of the method depicted in FIG. 4 may correspond to modules, realized by hard-wired logic circuits or customizable hardware, a program running on a processor, or any combination thereof, indicated by the baseline removal system 330.

At block 410 of FIG. 4, a signal is received from a signal source, such as the sample separator 310, which has generated the signal in accordance with a number of possible procedures, including chromatography, mass spectrometry, spectroscopy, electrophoresis, imaging, electronic measurements and the like. A weight function representing peak-free regions of the received signal is determined at block 420. The determined peak-free region weights of the received signal and the received signal are used in a smoothing spline fitting procedure at block 430, and the spline resulting from block 430 is denoted as an estimated baseline. The estimated baseline from block 430 is subtracted from the received signal at block 440, removing the estimated baseline. The processes indicated in blocks 420 and 430 are described in detail below with respect to FIGS. 5, 8 and 9, respectively. Further, in an embodiment, the processes indicated in blocks 420 and 430 are performed in parallel.

Figure 5:
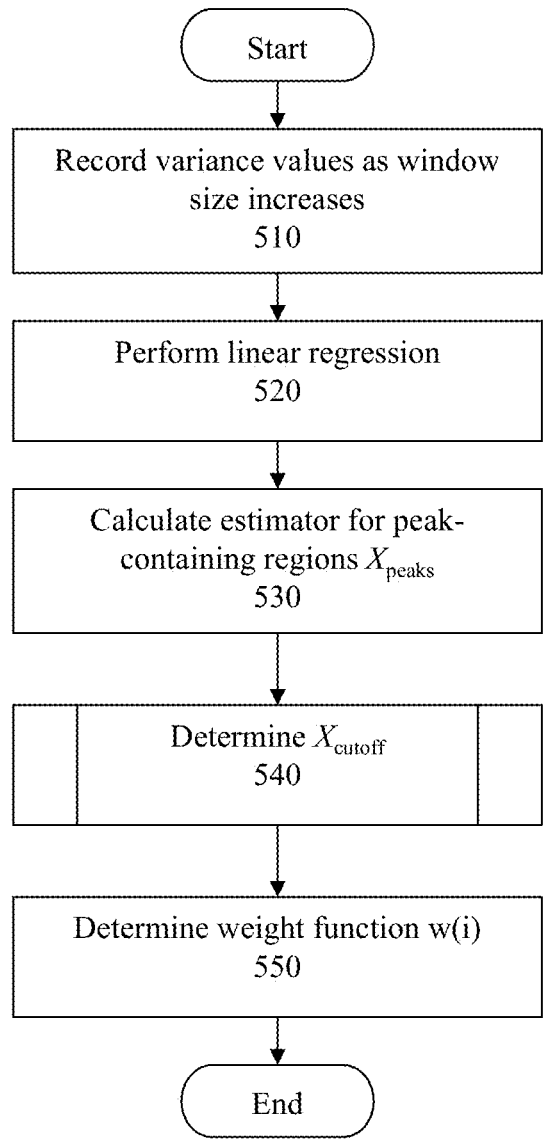
FIG. 5 is a flow diagram of a method for determining peak-free area estimator of FIG. 4, according to a representative embodiment.

FIG. 5 is a flow diagram illustrating a method for determining the weight function for peak-free regions of a signal, indicated by the process of block 420 of FIG. 4, according to a representative embodiment. The various operations of the method depicted in FIG. 5 may correspond to modules, realized by hard-wired logic circuits or customizable hardware, a program running on a processor, or any combination thereof, indicated by the baseline removal system 330.

In various embodiments, the determination of peak-free regions initially includes estimating peak-containing regions using variance of the signal, and more specifically, the rate of growth of the signal variance (e.g., blocks 510-530 of FIG. 5), further discussed with reference to FIGS. 6A and 6B, below. Unlike an estimator that uses slope of the signal, an estimator using the rate of growth of signal variance naturally takes into account noise present in the signal. Once the peak-free region estimator has been calculated, a weight function is built for baseline estimation using a previously calculated cutoff value (e.g., blocks 540-S550 of FIG. 5), further discussed with reference to FIG. 8, below. Generally, the peak regions have regression lines with higher slopes and higher intercepts than the baseline region.

Figures 6A, 6B:
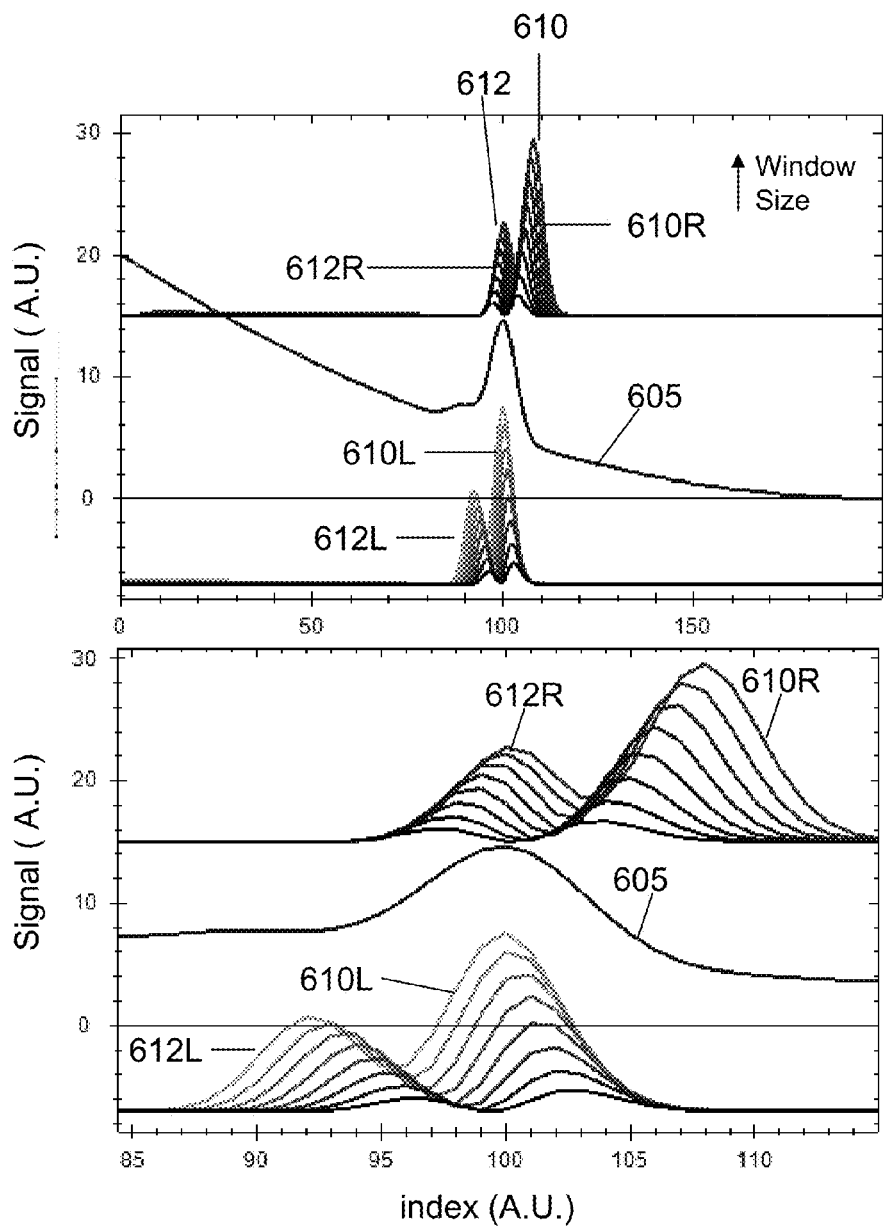
FIG. 6 is a graph showing variance of a signal, according to a representative embodiment.

FIGS. 6A and 6B show graphs depicting variances of a signal as a function of window size, according to a representative embodiment, showing rate of growth of signal variance. In particular, two synthetic peaks 610 and 612 of signal 605, shown in FIG. 6A, are fused and superimposed to a changing baseline. FIG. 6A also shows corresponding signal variances 610R/612R using windows that extend to the right of peaks 610 and 612, and corresponding signal variances 610L/612L using windows that extend to the left of peaks 610 and 612. FIG. 6B is a magnification of the signal 605 in the region in which the peaks 610 and 612 appear, showing variances 610R/612R and 610L/612L. The window sizes shown start at three, for example, and increase in unit increments. Although both contributions are actually added to determine the signal variances, 610R/612R and 610L/612L are shown separately for purposes of illustration. The location of the peak-containing region is thus apparent from the variance in the signal, as discussed below.

It is understood that alternative estimators for identifying peak containing regions may be incorporated, such as determining maximum range of values of the signal in the window, although using signal variance appears to be the most robust. For example, as the slope of the baseline increases, signal variance becomes non-negligible even in peak-free areas. When dealing with steep baselines and/or increasing amounts of noise, the distinction between peak-containing regions and peak-free regions may blur. However, the peak-containing regions and peak-free regions may still be distinguished based on the increase of the variance with increasing window sizes, which remains linear in baseline regions, but not in peak-containing regions.

Referring again to FIG. 5, estimating peak-containing regions begins with recording variance values of the signal as window size increases at block 510. Of course, it is understood that the mathematical form of the estimator, defined in terms of the rate of growth of the signal variance with increasing window size, may differ in various embodiments. The appropriate range of the window size is discussed below.

At block 520, a linear regression (e.g., a simple linear regression with one independent variable) of the variance values as a function of the window size is performed. Contributions $\beta_1$ and $\beta_2$ may be obtained from the following regression equation, where j denotes window sizes (j=3, ..., m), $y_j$ denotes values of the variance, and $\epsilon_j$ denotes the error in the variance due to noise:

$$y_j = \beta_1 + \beta_2 j + \epsilon_j \quad (1)$$

The value of the maximum window size m should be large enough to be statistically significant, but small enough to capture only local variations of the variance, the determination of which would be apparent. For example, m may be set in the range of 6-10, in a representative embodiment, to analyze both simulated and real signals. For peaks having fewer than six data points, for example, the window size may be reduced.

At block 530, values of the estimator of peak-containing regions $X_{peaks}$, defined along each point i in the signal, are determined in accordance with the following estimator:

$$X(i)_{peaks} = |\beta(i)_1| + \beta(i)_2 \quad (2)$$

Although both peak-free regions and peak-containing regions will have a variance that tends to shrink to zero with decreasing window size, the variance will rarely be zero in peak-containing regions. Also, while equation (2) shows a representative embodiment in which the contributions $\beta(i)_1$ and $\beta(i)_2$ are simply added, any linear combination or monotonic function of the two may provide similar results. Thus, block 530 yields a set of peak region values $X_{peaks}$, which are estimator values corresponding to each point i of the signal.

Figure 7A:
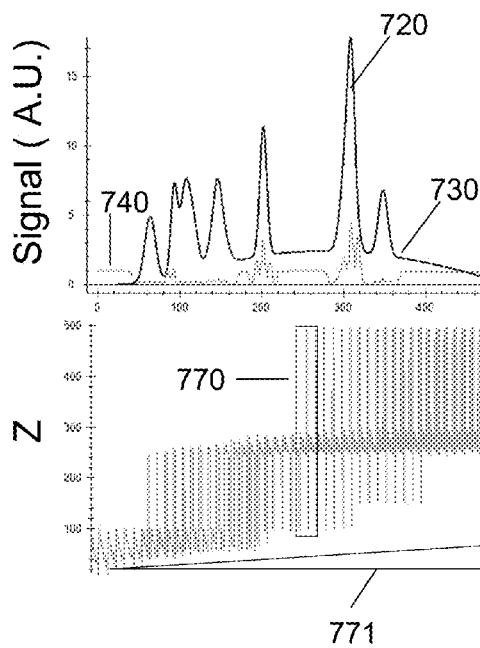
FIGS. 7A-7D are graphs showing determination of weight functions, according to a representative embodiment.

FIGS. 7A-7D are graphs showing peak-free and peak-containing regions, according to a representative embodiment. Referring to FIG. 7A, curve 720 depicts a sample signal having multiple peaks. The signal may be synthetic or may result from various processes, such as chromatography, mass spectrometry, spectroscopy, electrophoresis, imaging, electronic measurements or the like. The depicted signal 720 is a one-dimensional signal, although it is understood that the process may be generalized to accommodate two-dimensional signals, as well. Curve 730 depicts the peak region values $X_{peaks}$, for example, derived according to equation (2) in block 530, above. As shown, the curve 730 depicting peak region values $X_{peaks}$ tends to follow the baseline (having a value of approximately 0.525) in non-peak regions and to spike in peak regions of the signal curve 720. Curve 740 of FIG. 7A depicts a baseline weight function, which is determined in accordance with blocks 540-550 of FIG. 5, discussed below.

More particularly, peak-containing regions, in which the variance of the signal, $\sigma^2$, grows non-linearly and at a lower rate than a linear function, tend to have values of the first contribution $|\beta(i)_1|$ of equation (2) departing from zero. On the contrary, the rate of growth of $\sigma^2$ in peak-free regions is approximately linear, and $\beta(i)_1$ tends to have negligible values. Meanwhile, the second contribution $\beta(i)_2$ provides the slope of the regression line previous mentioned, which also tends to be higher in peak-containing regions compared to peak-free regions (the slope is always positive).

Figure 7B:
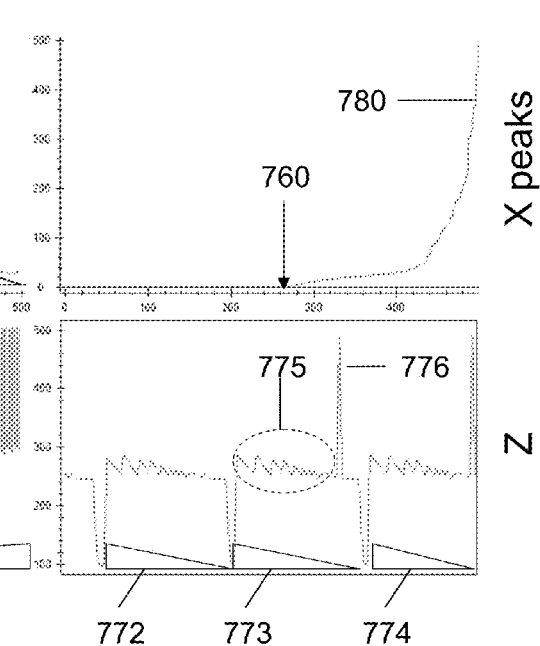

To build the peak-free weight function, peak region values $X_{peaks}$ are transformed into quantities having values of (0, 1), which can be used as weights to evaluate the presence (or absence) of peaks. To accomplish this, a cutoff value of the peak region values $X_{peaks}$ is determined at block 540 of FIG. 5, indicated by $X_{cutoff}$. The cutoff value $X_{cutoff}$ is where statistically significant departures from zero begin to occur, shown for example at location 760 of curve 780 in FIG. 7B. Curve 780 of FIG. 7B is an example of peak region values $X_{peaks}$ sorted in ascending order. The cutoff value $X_{cutoff}$ of the peak region values $X_{peaks}$ may be reliably determined in various manners, since baseline estimation is robust with respect to the precise value of cutoff values.

Figure 8:
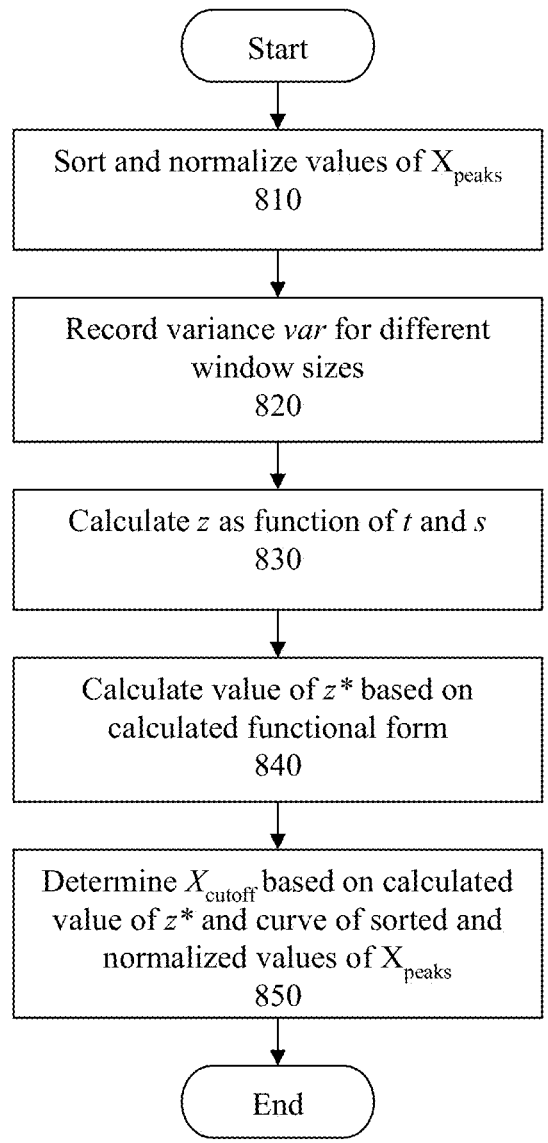
FIG. 8 is a flow diagram of a method for determining a cutoff value of peak region values, according to a representative embodiment.

FIG. 8 is a flow diagram illustrating an example of a process for determining a cutoff value $X_{cutoff}$, according to a representative embodiment, indicated by the process of block 540 of FIG. 5. The various operations of the method depicted in FIG. 8 may correspond to modules, realized by hard-wired logic circuits or customizable hardware, a program running on a processor, such as processor 330, or any combination thereof.

Referring to FIG. 8, after the peak region values $X_{peaks}$ have been calculated, the cutoff value $X_{cutoff}$ may be determined by first sorting the peak region values $X_{peaks}$ in ascending order and normalizing the sorted the peak region values $X_{peaks}$ to the length of the data at block 810. As stated above, curve 780 of FIG. 7B is an example of peak region values $X_{peaks}$ sorted in ascending order. Values of the variance var of values obtained in block 810 are then recorded over moving windows of a given size s at block 820. Recording the variance var may be accomplished by sliding the window over each point along the sorted list of peak region values $X_{peaks}$.

At block 830, values of point z are calculated for all possible values of threshold t and window sizes s. A threshold t is specified as a number that can take values between one and a fraction of the total length of the data (e.g., any relatively large number). For a given threshold t and a given window size s, a point z* is calculated at block 840 based on the functional form from block 830. The cutoff value $X_{cutoff}$ may then be determined at block 850 based on the calculated value of z* and the curve of the sorted and normalized values of the peak region values $X_{peaks}$. Point z* must satisfy the following relationship, where $var(s_z)$ is the variance of a window of size s starting at point z in the sorted series:

$$var(s_z) > t \, var(s_{z+1}) \quad (3)$$

Figure 7C:
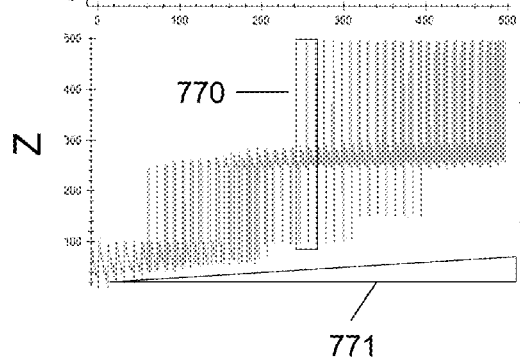

FIG. 7C indicates temporary cutoffs calculated with intervals of increasing stringency and decreasing window size within a given stringency. More particularly, FIG. 7C is a plot of values of points z (along the vertical axis) for all possible values of threshold t and window sizes s. In this figure, points z are calculated for increasing values of the threshold t, indicated by linearly increasing value 771, where for a given value of t, decreasing values of s are explored. Since each point z is a function of two variables, t and s, the curve in FIG. 7C shows all values of s corresponding to each value of t for each point z. When the value of point z is equal to the length of the dataset (the first occurrence being highlighted by rectangle 770 in FIG. 7C), it means that no point in the sorted list of the peak region values $X_{peaks}$ satisfies formula (3), which will always happen as t increases, for a large enough value of t. This value of point z is referred to as z*, and is determined at block 840 of FIG. 8. Decreasing window size amounts to looking for changes locally, or in other words, making the comparison of formula (3) more stringent.

Figure 7D:
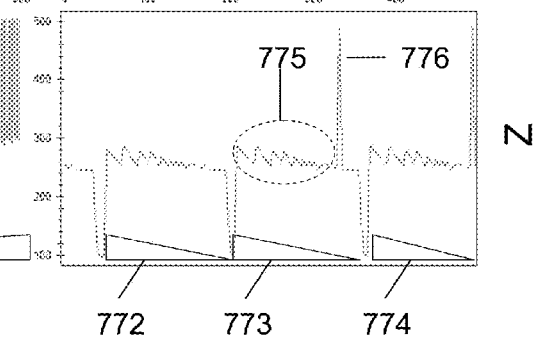

FIG. 7D is a zoom or magnification of the region of interest 770, showing more detail, where a first spike 776 large enough to be substantially equal to the length of the data (e.g., 500 in the depicted example) appears for the first time. As indicated by linearly decreasing values 772-774, the values of s go from highest to lowest for each value of t. To determine cutoff value $X_{cutoff}$, the value preceding the breakdown of formula (3), designated point z*, is simply estimated at block 840, which is approximately 260, corresponding to the point 760 of curve 780 in FIG. 7B. The values of z preceding the breakdown of formula (3) are indicated by dotted oval 775 in FIG. 7D, for example. Thus, the final cutoff value $X_{cutoff}$ is calculated at block 850 for the peak region values $X_{peaks}$ in the sorted list of FIG. 7B evaluated at a point determined in FIGS. 7C and 7D.

In the representative implementation, the first quartile of the distribution of points preceding the breakdown of formula 3, e.g., formed by points within the dotted oval 775, is used, which works well for diverse baselines and peak configurations (e.g., involving different peak numbers and different degrees of overlap). This quartile may then be used as the index in the sorted list (block 810) to calculate the final value of $X_{cutoff}$, as shown in block 850.

Referring again to FIG. 5, once the cutoff value $X_{cutoff}$ of the peak region values $X_{peaks}$ has been determined, e.g., in accordance with the process of FIG. 8, a peak-free region or baseline weight function w(i) may be calculated at block 550 as follows, where i represents points along the signal:

$$w(i) = e^{-\frac{X(i)_{peaks}}{X_{cutoff}}} \quad (4)$$

Again, baseline estimation is robust against changes in this function, and variants (e.g., involving the use a hyperbolic tangent in conjunction with a cutoff) could be used. The values of the baseline weight function w(i) corresponding to the example are indicated by curve 740 of FIG. 7A. As shown, the baseline weight function w(i) has values that are arbitrarily close to 1 in each peak-free region and arbitrarily close to 0 in each peak-containing region. Therefore, when the signal is multiplied by the weight function w(i), the peak-containing regions are effectively suppressed, leaving the peak-free regions subject to spline fitting, discussed below. In an embodiment, the weight function w(i) is applied to the signal in the same process as the spline fitting, such that determination of the peak-free regions and the spline fitting are sub-operations of a parallelized fitting procedure.

Referring again to FIG. 4, after the weight function (e.g., estimator) that denotes the peak-free regions of the received signal (i.e., containing the baseline) is determined by the procedure indicated at block 420 (described above), the signal weighted in accordance with the weight function is fitted by a smoothing spline procedure at block 430 to provide an estimated baseline. That is, the next process is to interpolate a smooth curve that effectively includes the peak-free regions of the signal obtained by multiplying the signal by the weight function, which may be achieved using piecewise polynomials, for example. Generally, piecewise polynomials are used since it is computationally more efficient to approximate a well behaved function with multiple low order polynomials than with a single higher order polynomial. At block 440 of FIG. 4, the estimated baseline is subtracted from the received signal, in accordance with various apparent techniques, to obtain the actual signal.

Piecewise polynomials interpolate data (e.g., from the signal) along a finite series of intervals. The points defining these intervals are called knots. In an embodiment, splines are used as the piecewise polynomials, since splines are less erratic at boundaries and have smaller fluctuations than standard polynomials because they satisfy the constraint that all associated derivatives are continuous at the knots. In an embodiment, cubic splines are used, which are cubic polynomials satisfying continuity of the function, the first slope and the curvature at the knots.

Figure 2:
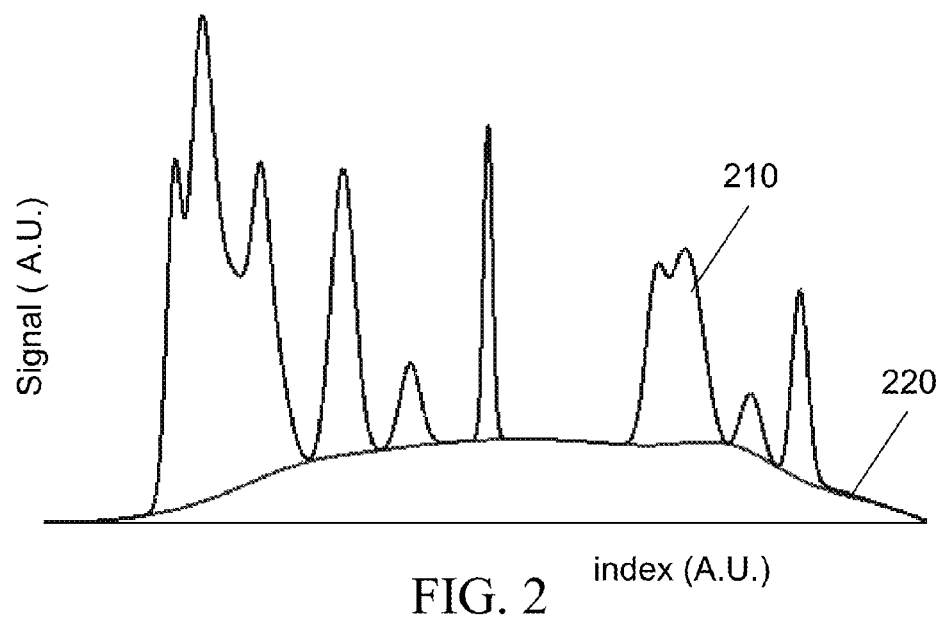
FIG. 2 is a graph showing a conventional signal with baseline that overfits.

When fitting scattered data of the signal data, there are two goals: fidelity and smoothness. Fidelity means that the interpolated smooth curve of the estimated baseline closely follows the peak-free regions of the signal data. Smoothness means that the estimated baseline should not overfit peak-containing regions, which have not been selected from the signal data, as depicted by the asterisks in FIG. 2, for example. Fidelity and smoothness are incompatible to some degree, and therefore a compromise is needed in the form of an optimization. For example, when fitting scattered data using a spline, a function g may be defined as follows, where $(y_i, x_i)$ is a data set consisting of N points, S is the cubic spline, and $\lambda$ is a positive real number referred to as the "smoothing factor":

$$g(\lambda) = \sum_{i=1}^{N} (y_i - S(x_i))^2 + \lambda \int S''(t)^2 dt \quad (5)$$

The first term in the right side of equation (5) (i.e., $(y_i - S(x_i))^2$) is a standard term used in linear regression to penalize departures of the spline from the data set. The second term on the right side of equation (5) (i.e., $\lambda \int S''(t)^2 dt$) penalizes high curvature of the spline or lack of smoothness. The smoothing factor $\lambda$, discussed below, defines how much weight smoothness has over data fidelity. When $g(\lambda)$ is optimized for a given value of the smoothing factor $\lambda$, a "smoothing spline" will be obtained, as described for example in Reinsch, *Smoothing by Spline Functions*, NUMBER. MATH. 10: 177-183 (1967), the contents of which are hereby incorporated by reference. For a smoothing factor $\lambda \ll 1$, the resulting smoothing spline will fit as many data points as possible, while for large values of the smoothing factor $\lambda$, a smooth curve that passes through the center of the scattered data will be obtained.

When optimizing equation (5), it is customary to use natural cubic splines, which have zero curvature at both ends of the data set (i, where i=0, N) because the cubic spline minimizes the second term of the right side of equation (5). Only portions of the data where weights are not negligible are fit, thus fitting only peak-free regions of the signal as opposed to the entire signal. In this case, $g(\lambda)$ from equation (5) may be minimized as follows, where w(i) are the weights determined according to equation (4) (e.g., as indicated by line 740 of FIG. 7A):

$$g(\lambda) = \sum_{i=1}^{N} (y_i - S(x_i))^2 w(i) + \lambda \int S''(t)^2 dt \quad (6)$$

Equation (6) does not include a penalty for situations in which $y(i) - S(x_i) < 0$ and $w(i) \ll 1$. In other words, where weights w(i) are negligible, the baseline may end up having higher values than the real signal, and thus baseline subtraction may result in a negative net signal. To prevent equation (6) from generating a negative net signal in regions where weights w(i) are negligible, w(i) may be provided a (predetermined) finite value in all points where the relationship $S(i) > y_i$ holds. The finite value provided w(i) need not be precise, although normally the finite value should be in the range of 1 to 100. Finite values larger than 1 appropriately penalize the situations in which $y(i)-S(x_i) < 0$ and $w(i) \ll 1$, while finite values less than 100 avoid slight underfitting of the baseline, e.g., when large amounts of white noise are present in the signal.

Figure 9:
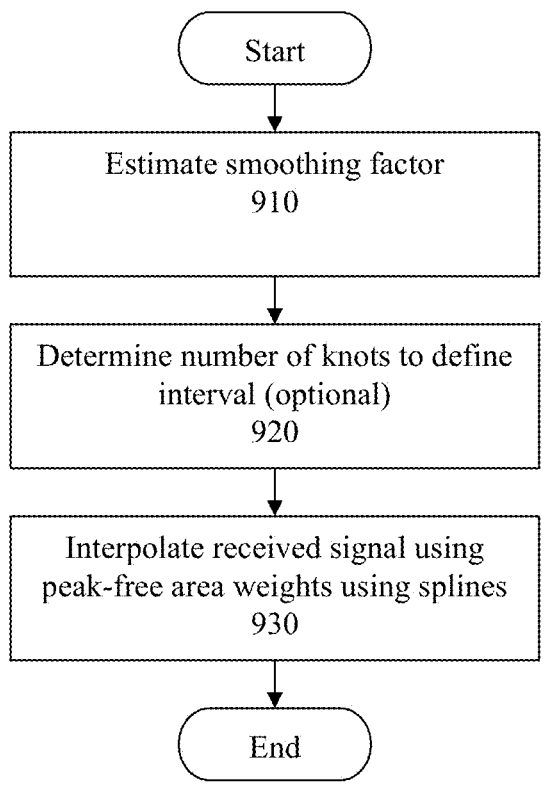
FIG. 9 is a flow diagram of a method for estimating a baseline of FIG. 4, according to a representative embodiment.

FIG. 9 is a flow diagram illustrating fitting the weighted signal indicated by the process of block 430 in FIG. 4 using equation (6), according to a representative embodiment. The various operations of the method depicted in FIG. 9 may correspond to modules, realized by hard-wired logic circuits or customizable hardware, a program running on a processor, or any combination thereof, indicated by the baseline removal system 330.

Referring to FIG. 9, the smoothing factor λ is determined in block 910. In an embodiment, the value of the smoothing factor λ is set in a self-consistent manner, such as in accordance with a generalized cross-validation procedure, as described, for example, in Craven et al., *Smoothing Noisy Data with Spline Functions: Estimating the Correct Degree of Smoothing by the Method of Generalized Cross-Validation*, NUMBER. MATH. 31:377-403 (1979) (hereinafter Craven et al.), the contents of which are hereby incorporated by reference.

However, the cross validation procedure may be computationally expensive, particularly for batch or interactive processing of very long signals. Therefore, in an alternative embodiment, the smoothing factor λ may be estimated. For example, an automated routine may estimate the value of the smoothing factor λ from the curvature of the peak-free regions of the signal (i.e., the regions of the signal where the weight function w(i) is close enough to 1, as discussed above). First, for each contiguous peak-free region of the signal, such as the four peak-free regions shown in the example of FIG. 7A, a curvature g" of each region through the largest possible five-point stencil (e.g., as defined by equation (7)), is numerically estimated in accordance with the following equation, where x is a point in the middle of the region, h is the segment length divided by five, and f:

$$g'' \approx \frac{-f(x+2h)+16f(x+h)-30f(x)+16f(x-h)-f(x-2h)}{12h^2} \quad (7)$$

While a five point stencil provides a robust estimate of the curvature, any other finite difference approximation of the curvature may be used, such as the following:

$$g'' \approx \frac{f(x+h)+2f(x)+f(x-h)}{h^2} \quad (8)$$

Next, among all of the segments examined, a maximum max{|g"|} is determined. The smoothing factor λ is then defined to be proportional to 1/max{|g"|}. Since max{|g"|} among the segments may be arbitrarily low due to noise, a functional form of the smoothing factor λ may be selected that has an upper bound as follows, where $\epsilon = 1/1000$ (the chosen value of 1000 being arbitrary):

$$\lambda = \frac{1}{(\max\{|g''|\}+\epsilon)} \quad (9)$$

Other functions that are proportional to the inverse of the curvature may likewise be used.

Notably, once the peak-free regions of the signal are determined through the baseline weight function w(i), the optimization of equation (6) is substantially insensitive to a precise value of the smoothing factor λ. This may occur, for example, for variations of four to five orders of magnitude. Therefore, the estimation of the smoothing factor λ here proposed is sufficient, and is a computationally less expensive alternative to the generalized cross-validation procedure, for example, as described in Craven et al.

Referring again to FIG. 9, at block 920, the number of knots is determined for defining the smoothing splines S of equation (6). The number of knots is the number of pieces of the piecewise polynomial that will form the baseline. A large number of knots is generally desirable, since it is unknown, a priori, how fast the baseline will change from the beginning to the end of the signal. However, because the number of variables to minimize is equal to the number of knots, the computational cost rapidly increases with the number of knots, which factors in favor of fewer knots. Also, equation (6) prevents the curvature of the spline from rising independently of the number of knots, so a large number of knots is not necessarily needed.

Therefore, in an embodiment, five knots equally spaced along the domain of the signal are used, and up to 15 knots provides essentially indistinguishable results, for example. In alternative embodiments, the knots are not equally spaced, but rather may be distributed with a density proportional to an absolute value of curvature g" calculated in equation (7), for example.

At block 930, the signal data is interpolated along the knots using splines, e.g., in accordance with equation (6), above. That is, function g is defined for data set $(y_i, x_i)$ of the signal consisting of N points in each cubic spline S. The resulting series of cubic splines provides the smoothed, interpolated curve representing the estimated baseline of the signal. Referring again to FIG. 4, this smoothed, interpolated curve is subtracted from the signal at block 440 to remove the estimated baseline.

FIGS. 10A-10D are graphs showing an example of determining and removing baselines, according to a representative embodiment. In the depicted embodiment, the minimization of equation (6) was performed using Particle Swarm Optimization, although other optimization methods may be used, as discussed above. Generally, Particle Swarm Optimization is a stochastic, population-based evolutionary computer algorithm used for optimization. An ensemble of particles, called "swarm," is modeled multidimensionally, such that each particle has a position and a velocity. The particles move through multidimensional space sampling the function that they are optimizing. Each particle remembers its best position and is aware of its neighboring particles' best positions (referred to as "social cognition"), respectively. Swarm members communicate with each other and adjust their trajectories based on the quality of their positions. As movement of the swarm progresses, the fitness of the global solution converges to a global optimum. By using Particle Swarm Optimization, the determination of peak-free regions and the fitting procedure may be parallelized, e.g., for efficient analysis of long signals. Testing indicates that normalizing the first term of the right hand side of equation (6) by the length of the signal and using absolute values of errors instead of squared differences of errors made the peak removal process slightly more consistent for a noisy signal which changes in length. For example, signal lengths tested ranged from 100 to 10,000 points.

Referring to FIGS. 10A-10D, Gaussian peaks of different heights and degree of overlap were randomly generated. The overlap among two consecutive peaks was defined as the area of the smaller peak falling under the curve of the larger of the two peaks. The maximum height of each peak and the window of allowed overlap among peaks were specified by the user. The absolute amount of white noise added to the signal was also user specified in the testing. Different baseline types were added to the indicated number of peaks before baseline estimation. Automated calculations of the cutoff for the weights of the weight function and the value of the smoothing factor $\lambda$ are shown for each signal. Signals are shown by curves 1010a-1010d, peak region values $X(i)_{peaks}$ determined from equation (2) are shown by curves 1020a-1020d, weight factors w(i) determined from equation (4) are shown by curves 1030a-1030d, and the resulting calculated baselines are shown by curves 1040a-1040d, respectively. FIGS. 10A-10D show that the baseline removal process does not overfit signals having highly overlapped peaks.

Figures 11A, 11B:
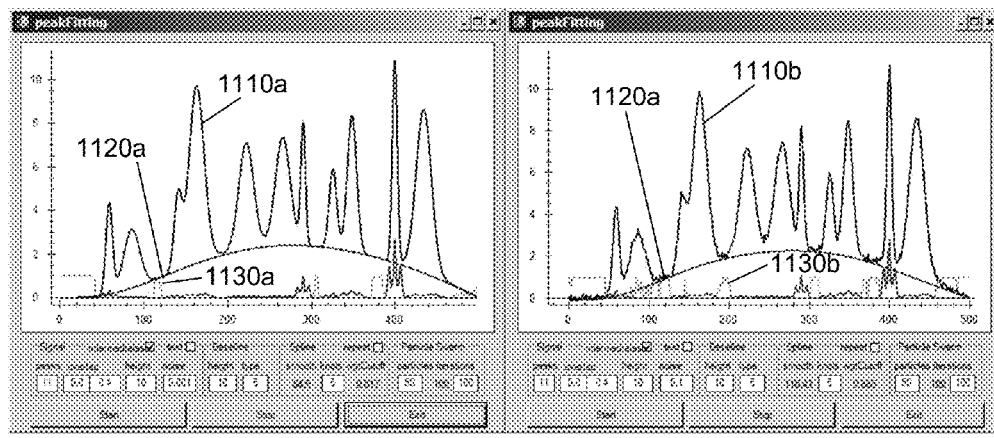
FIGS. 11A-11B are graphs showing estimation of a baseline for a signal having noise, according to a representative embodiment.

In addition, testing indicated that the peak estimator indicated by equation (2) is robust to noise, as shown, for example, in FIGS. 11A and 11B. In particular, FIG. 11A shows a signal curve 1110a and corresponding baseline curve 1120a, obtained through baseline estimation performed in accordance with an embodiment of the baseline removal process, and FIG. 11B shows a signal curve 110b with a 100 fold increase in noise level and corresponding baseline curve 1120b, obtained through the baseline estimation. As shown in FIG. 11B, the estimated baseline curve 1120b indicates negligible distortion as compared to the estimated baseline 1120a, regardless of the substantial increase in the noise level.

Notably, because of signal degradation, there is some growth in peak-free regions where weight factors w(i) are non-negligible, indicated by curve 1130b of FIG. 11B, as compared to curve 1130a of FIG. 11A. Therefore, eventually, as peaks become excessively overcrowded or additional increases in noise further degrade the signal 1110b, the baseline estimation may begin to overfit. In an embodiment, the signal 1110b having the excessive noise level may be denoised in a manner preserving first and second derivatives, for example, by using a Savitzky-Golay filter, described by Savitzky et la., *Smoothing and Differentiation of Data by Simplified Least Squares Procedure*, ANAL. CHEM., 36 (1964), pp. 1627-1639, the contents of which are hereby incorporated by reference.

Figure 12A:
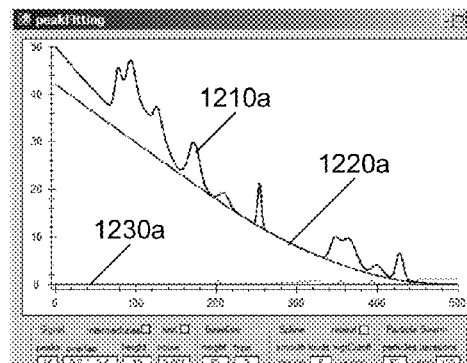
FIGS. 12A-12D are graphs showing iterative estimation of a baseline, according to a representative embodiment.
Figure 12B:
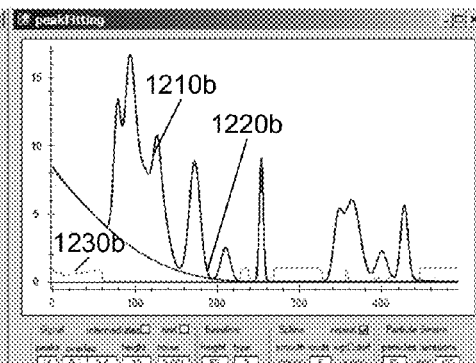

In a representative embodiment, the baseline removal process may be applied two or more times, e.g., by consecutively subjecting the baseline-subtracted signal obtained by a previously applied baseline remove process to the baseline removal process. For example, when baselines change too fast, a single application of the baseline removal process discussed above may not capture portions of the baseline that have high slope. This may result in underfitting the signal, as shown in FIG. 12A, for example. However, as shown in FIG. 12B, by applying the baseline removal process iteratively, the missing portions of the baseline are recovered without overfitting the portions of the signal that were accurate after the first pass.

More particularly, FIG. 12A is a graph showing a signal curve 1210a having a fast changing baseline curve 1220a, which can not be removed by the baseline removal process, e.g., indicated by the substantially flat weight factor curve 1230a. FIG. 12B is a graph showing the signal curve 1210b and corresponding estimated baseline curve 1220b after subjecting the signal curve 1210a remaining after baseline subtraction to a second baseline removal process. As shown, the resulting weight factor curve 1230b indicates the peak-free regions for establishing the baseline curve 1220b.

Figure 12C:
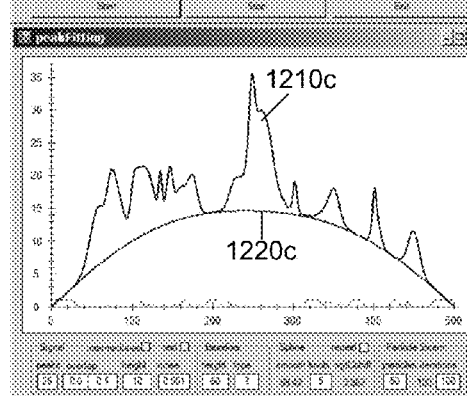
Figure 12D:
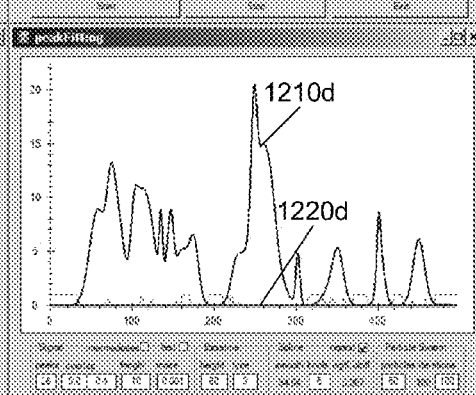

Notably, when the baseline removal process is repeated for baselines that do not underfit or overfit to begin with, there are no deleterious effects, as shown in FIGS. 12C and 12D, for example. That is, FIG. 12C is a graph showing a signal curve 1210c having an accurately determined baseline curve 1220c. FIG. 12D is a graph showing the signal curve 1210d and corresponding estimated baseline 1220d after subjecting the signal 1210c remaining after baseline subtraction to a second baseline removal process, resulting in no overfitting. Thus, applying the baseline removal process twice incurs double the computational cost, but effectively treats fast changing baselines without risk of negative effects.

FIGS. 13A-13D show baseline estimates of the baseline removal process, according to representative embodiments. In particular, the baseline removal process was applied to curves 1310a-1310d of experimental signals obtained from gas chromatography of kerosene samples, according to representative embodiments. The chromatograms of FIGS. 13A-13D are separations along the second (hydrophobic) dimension of a two-dimensional chromatography experiment. Corresponding peak region values $X(i)_{peaks}$ determined from equation (2) are shown by curves 1320a-1320d, weight factors w(i) determined from equation (3) are shown by curves 1330a-1330d, and the resulting calculated baselines are shown by curves 1340a-1340d (beneath the peak-containing regions of the signal curves 1310a-1310d), respectively. Also, FIG. 13A includes insert 1345, which includes a magnification of the lower portion of the signal curve 1310a and baseline curve 1340a.

The baseline estimate curves 1340a-1340d of FIGS. 13A-13D are based on different fractions 623, 953, 866 and 790, respectively, corresponding to the second dimension in the two-dimensional gas chromatography separation of the kerosene. In particular, the kerosene sample undergoes a two-dimensional gas chromatography separation, and the elution corresponding to time points of the separation in the first dimension are called "fractions." In this case, each fraction is further separated through a second separation, or dimension. The horizontal axis of each of FIGS. 13A-13D corresponds to the time course of the second separation. The fractions analyzed were selected by visual inspection to have the highest degree of peak overlap among more than 1500 fractions available. The resulting baseline estimate curves 1340a-1340d demonstrate that no overfitting takes place in the experimental signals.

Figure 14:
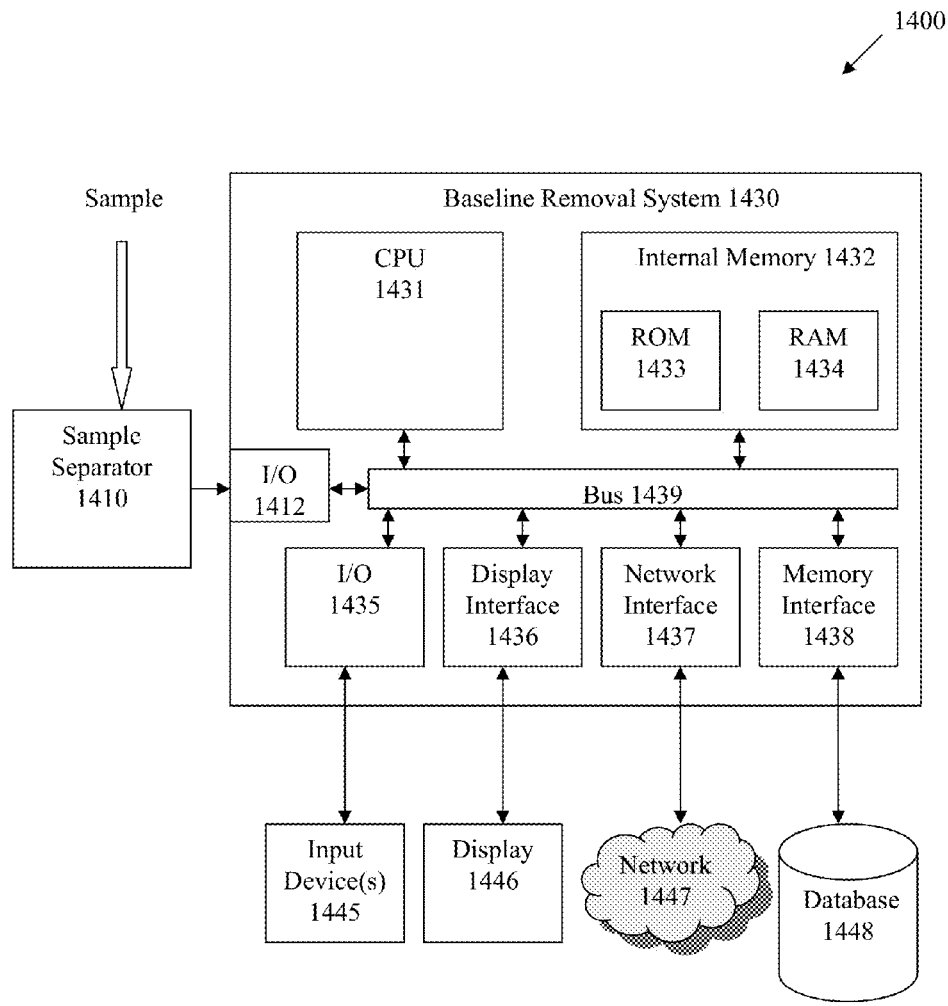
FIG. 14 is a functional block diagram illustrating a system for removing baseline of a signal, according to a representative embodiment.

FIG. 14 is a functional block diagram illustrating a system 1400, according to a representative embodiment. The system 1400 may be any system for receiving and processing one-dimensional or two-dimensional signals, such as signals produced in accordance with chromatography, mass spectrometry, spectroscopy, electrophoresis, imaging, electronic measurements and the like. The system 1400 may represent an LC/MS system, which generally combines separation functionality of liquid chromatography with mass analysis ability of mass spectrometry.

In the depicted representative embodiment, the system 1400 includes a sample separator 1410 and a baseline removal system 1430. The sample separator 1410 receives samples, which may include various mixtures molecules (e.g., peptides, proteins, or the like) to be identified. As stated above, the samples may be separated by the sample separator 1410 via various types of separation processing to reduce the complexity of the mixture and to isolate to the extent possible individual compounds contained within sample. Isolation may occur spatially or temporally, for example. The sample separator 1410 may perform separation processing in accordance with any appropriate separation technique, including two-dimensional gel electrophoresis and LC/MS, and may be implemented in part using a microfluidic device, for example. The sample separator 1410 provides (one-dimensional or two-dimensional) signals to the baseline removal system 1430, in various embodiments.

The baseline removal system 1430 performs processing on the received signals, e.g., from sample separations, including the baseline removal process, in accordance with various embodiments discussed below. The baseline removal system 1430 may be a computer processor, for example, and includes central processing unit (CPU) 1431, internal memory 1432, bus 1439 and interfaces 1435-1438, and is configured to interface with the sample separator 1410 through a respective interface 1412, which may be a universal serial bus (USB) interface, an IEEE 1394 interface, or a parallel port interface, for example. As stated above, it is understood that, although depicted separately, the baseline removal system 1430 may be included within the sample separator 1410, in various embodiments.

With respect to the baseline removal system 1430, the internal memory 1432 includes at least nonvolatile read only memory (ROM) 1433 and volatile random access memory (RAM) 1434, although the internal memory 1432 may be implemented as any number, type and combination of ROM and RAM, and may provide look-up tables and/or other relational functionality. In various embodiments, the internal memory 1432 may include a disk drive or flash memory, for example. Further, the internal memory 1432 may store program instructions and results of calculations or summaries performed by CPU 1431, discussed below.

The CPU 1431 is configured to execute one or more software algorithms to perform the baseline removal process of the embodiments described herein, in conjunction with the internal memory 1432. In various embodiments, the CPU 1431 may also execute software algorithms to control the basic functionality of the system 1400. The CPU 1431 may include its own memory (e.g., nonvolatile memory) for storing executable software code that allows it to perform the various functions. Alternatively, the executable code may be stored in designated memory locations within internal memory 1432. The executable code may be written in C, C++ or other capable programming language. The CPU 1431 executes an operating system, such as a Windows® operating system available from Microsoft Corporation, a Linux operating system, a Unix operating system (e.g., Solaris™ available from Sun Microsystems, Inc.), or a NetWare® operating system available from Novell, Inc. The operating system may control execution of other programs, including programs that cause sample separator 1410 to perform such operations as collection and separation of samples and output of corresponding signals.

In an embodiment, a user and/or other computers may interact with the baseline removal system 1430 using input device(s) 1445 through I/O interface 1435. The input device(s) 1445 may include any type of input device, for example, a keyboard, a track ball, a mouse, a touch pad or touch-sensitive display, and the like. Also, information may be displayed by the baseline removal system 1430 on display 1446 through display interface 1436, which may include any type of graphical user interface (GUI), for example. The displayed information includes the processing results obtained by the CPU 1431 executing the method of peak detection, described herein.

The processing results of the CPU 1431 may also be stored in the database 1448 through memory interface 1438. The database 1448 may include any type and combination of volatile and/or nonvolatile storage medium and corresponding interface, including hard disk, compact disc (e.g., CD-R/CD/RW), USB, flash memory, or the like. The stored processing results may be viewed, e.g., on the display 1446, and/or further processed at a later time. Also, the processing results may be provided to other computer systems connected to network 1447 through network interface 1437. The network 1447 may be any network capable of transporting electronic data, such as the Internet, a local area network (LAN), a wireless LAN, and the like. The network interface 1247 may include, for example, a transceiver (not shown), including a receiver and a transmitter, that provides functionality for the system 1400 to communicate wirelessly over the data network through an antenna system (not shown), according to appropriate standard protocols. However, it is understood that the network interface 1437 may include any type of interface (wired or wireless) with the communications network, including various types of digital modems, for example. The baseline determination process is intended to determine and remove the baseline of a signal generated using a number of possible signal sources, including chromatography, mass spectrometry, spectroscopy, electrophoresis, imaging, electronic measurements and the like. In addition, the baseline determination process may determine and remove background signals, such as background illumination on an image, e.g., when the method is adapted to two-dimensional signals.

The various "parts" shown in FIG. 14 of the baseline removal system 1430 may be physically implemented using a software-controlled microprocessor, hard-wired logic circuits, or a combination thereof. Also, while the parts are functionally segregated for explanation purposes, they may be combined variously in any physical implementation.

As discussed above, baseline determination of the baseline removal process produces baselines that do not overfit the corresponding signals, even in the presence of congested or overcrowded peaks. Also, the baseline determination is automated and parameter-less, although a user may optionally control two underlying parameters, i.e., the smoothness factor and the weight cutoff, which may be useful when information about the nature of the sample/measurement provides meaningful constraints on the shape of the baseline. The main computational burden of the baseline determination (the calculation of peak free regions and a numerical optimization) is efficiently parallelized, making it well suited for long signals (e.g., a large number of points). Also, the baseline determination may be easily generalized and applied to two-dimensional signals, broadening its scope to baseline removal in multidimensional separations, for example, in LS/MS systems, and removal of background from images.

While specific embodiments are disclosed herein, many variations are possible, which remain within the concept and scope of the invention. Such variations would become clear after inspection of the specification, drawings and claims herein. The invention therefore is not to be restricted except within the scope of the appended claims.

What is claimed is:

1. A system for estimating a baseline of a signal, the system comprising:
a signal generator configured to generate a signal exhibiting a plurality of peaks and a baseline; and
a processor configured to perform operations comprising:

determining an estimator indicating at least one region of the signal that exhibits a peak, wherein the determining the estimator comprises recording values of a rate of growth of variance of the signal as a function of increasing window sizes, performing a regression of the values of the rate of growth of the signal variance, and determining the estimator based on results of the regression;

determining a weight indicating at least one region of the signal that does not exhibit a peak based on the estimator; and estimating the baseline of the signal based on the at least one region of the signal that does not exhibit a peak.

2. The system of claim 1, wherein the rate of growth of the variance of the signal is non-linear in the at least one region of the signal that exhibits a peak, and the rate of growth of the variance of the signal linear in the at least one region of the signal that does not exhibit a peak.

3. The system of claim 1, wherein estimating the baseline comprises determining a smoothing factor and fitting the signal using smoothing splines and the smoothing factor.

4. The system of claim 1, wherein determining the weight further is further based on a cutoff value of the estimator at which a statistically significant departure from zero occurs.

5. The system of claim 1, wherein the regression comprises a linear regression having one independent variable.

6. The system of claim 5, wherein performing the linear regression comprises determining regression parameters $\beta_1$ and $\beta_2$ of the linear regression according to the following regression equation:

$$y_j = \beta_1 + \beta_2 j + \epsilon_j$$

wherein $y_j$ are the values of the signal variance, j denotes window size and $\epsilon_j$ is error in the signal variance due to noise in the signal.

7. The method of claim 1, wherein the window sizes increase in unit increments.

8. A system for estimating a baseline of a signal, the system comprising:

a signal generator configured to generate a signal exhibiting a plurality of peaks and a baseline; and a processor configured to perform operations comprising:

determining an estimator indicating at least one region of the signal that exhibits a peak, wherein the determining the estimator comprises recording values of a rate of growth of variance of the signal, performing a linear regression of the values of the rate of growth of the signal variance, the linear regression having one independent variable, and determining the estimator based on results of the regression;

determining a weight indicating at least one region of the signal that does not exhibit a peak based on the estimator; and estimating the baseline of the signal based on the at least one region of the signal that does not exhibit a peak, wherein performing the linear regression comprises determining regression parameters $\beta_1$ and $\beta_2$ of the linear regression according to the following regression equation:

$$y_j = \beta_1 + \beta_2 j + \epsilon_j$$

wherein $y_j$ are the values of the signal variance, j denotes window size and $\epsilon_j$ is error in the signal variance due to noise in the signal, and wherein the estimator is indicated by peak region values $X_{peaks}$, defined along each point i in the signal as follows:

$$X(i)_{peaks} = |\beta(i)_1 + \beta(i)_2|$$

wherein the regression parameter $\beta(i)_1$ indicates the rate of growth of the signal variance and the regression parameter $\beta(i)_2$ indicates a slope of the linear regression.

9. The system of claim 8, wherein absolute values of the regression parameter $\beta(i)_1$ depart from zero in the at least one region of the signal that exhibits a peak, and values of the regression parameter $\beta(i)_1$ are negligible in the at least one region of the signal that does not exhibit a peak.

10. The system of claim 8, wherein determining a weight comprises:

determining a cutoff value of the peak region values $X_{peaks}$ at which a statistically significant departure from zero occurs, the cutoff value being indicated by weight cutoff value $X_{cutoff}$; and determining the weight based on the peak region values $X_{peaks}$ and the weight cutoff value $X_{cutoff}$.

11. The system of claim 10, wherein determining the weight based on the peak region values $X_{peaks}$ and the weight cutoff value $X_{cutoff}$ comprises determining the weight according to the following equation:

$$w(i) = e^{-\frac{X(i)_{peaks}}{X_{cutoff}}}$$

12. A non-transitory computer readable medium storing a program, executable by a computer processor, for estimating a baseline of a signal, the program instructing the computer processor to perform operations comprising:

determining an estimator indicating at least one region of the signal that exhibits a peak, wherein the determining the estimator comprises recording values of a rate of growth of variance of the signal as a function of increasing window sizes, performing a regression of the values of the rate of growth of the signal variance, and determining the estimator based on results of the regression;

determining a weight indicating at least one region of the signal that does not exhibit a peak based on the estimator; and estimating the baseline of the signal based on at least the determined weight indicating the at least one region of the signal that does not exhibit a peak and a smoothing factor.

13. The computer readable medium of claim 12, wherein the rate of variance growth being non-linear in the at least one region of the signal that exhibits a peak, and the rate of variance growth being linear in the at least one region of the signal that does not exhibit a peak.

14. The computer readable medium of claim 13, wherein determining the estimator comprises:

recording values of the rate of variance growth;

performing a linear regression of the values of the rate of variance growth; and determining the estimator based on results of the linear regression.

15. The computer readable medium of claim 13, wherein determining the weight comprises determining the weight further based on a cutoff value of the estimator at which a statistically significant departure from zero occurs.

16. The computer readable medium of claim 12, wherein the window sizes increase in unit increments.

* * * * *

UNITED STATES PATENT AND TRADEMARK OFFICE
CERTIFICATE OF CORRECTION

PATENT NO. : 8,645,090 B2
APPLICATION NO. : 12/466031
DATED : February 4, 2014
INVENTOR(S) : Javier E. Satulovsky Page 1 of 1

It is certified that error appears in the above-identified patent and that said Letters Patent is hereby corrected as shown below:

On the title page, Item (56), under "Other Publications", in column 2, line 13, delete "Berstein" and insert -- Bernstein --, therefor.

In the Claims

In column 15, line 17, in claim 2, after "signal" insert -- is --.

In column 15, line 24, in claim 4, delete "further is further" and insert -- is further --, therefor.

In column 15, line 35, in claim 6, delete "$y_i$" and insert -- $y_j$ --, therefor.

In column 15, line 38, in claim 7, delete "method" and insert -- system --, therefor.

In column 15, line 65, in claim 8, delete "$y_i$" and insert -- $y_j$ --, therefor.

Signed and Sealed this
Twenty-seventh Day of May, 2014

Michelle K. Lee
*Deputy Director of the United States Patent and Trademark Office*